United States Patent [19]

Kanematu et al.

[11] Patent Number: 4,618,491

[45] Date of Patent: Oct. 21, 1986

[54] STABLE GEL COMPOSITION CONTAINING A CARBOXYMETHYL CELLULOSE SALT AND A PROCESS FOR THE PREPARATION OF THEM

[75] Inventors: Tetuo Kanematu; Yoshiaki Yamaguchi, both of Himeji, Japan

[73] Assignee: Daicel Chemical Industries Ltd., Osaka, Japan

[21] Appl. No.: 793,723

[22] Filed: Oct. 31, 1985

Related U.S. Application Data

[63] Continuation of Ser. No. 617,352, Jun. 5, 1984, abandoned.

[51] Int. Cl.⁴ .............................................. A61K 31/78
[52] U.S. Cl. ..................................................... 424/81
[58] Field of Search ........................................... 424/81

[56] References Cited

U.S. PATENT DOCUMENTS 4,309,414  1/1982  Inagi et al. .......................... 424/274

Primary Examiner—Stanley J. Friedman
Attorney, Agent, or Firm—Sheldon Palmer

[57] ABSTRACT

Stable gel compositions comprising a water-soluble salt of carboxymethyl cellulose wetted by or dispersed in a hydrophilic organic liquid such as glycerol, methanol acetone or the like and an aqueous solution of a water-soluble polyvalent metal salt such as potassium alum, ferric chloride, cupric chloride or the like, which are useful as bases for many preparations of medicines, cosmetics and the like.

8 Claims, No Drawings

STABLE GEL COMPOSITION CONTAINING A CARBOXYMETHYL CELLULOSE SALT AND A PROCESS FOR THE PREPARATION OF THEM

This application is a continuation of application Ser. No. 617,352, filed 6/5/84, now abandoned.

BACKGROUND OF THE INVENTION

1. Field of the Invention

The present invention relates to stable gel compositions containing a water-soluble salt of carboxymethyl cellulose (hereinafter abbreviated as CMC), particularly, uniform and stable gel compositions containing CMC which are useful for many purposes including preparation of medicines, cosmetics and the like, and a process for the preparation of such compositions.

2. Brief Description of the Prior Art

It is known that CMC is precipitated or gelated promptly by most polyvalent metal salts. In many instances, however, the product becomes fibrous or granular precipitates or solid massive precipitates and so the whole system becomes non uniform which is far from a uniform gel such as konnyaku jelly (devil's tongue jelly) or pudding.

For the formation of a uniform gel of synthetic macromolecules, there is a known process in which there is used a gelating agent that is hardly soluble in water, such as basic aluminum acetate, (Japanese Patent Laid-open No. Sho 54-106598). When this known process is applied to CMC, however, CMC is gelated on the surface of the gelating agent to form a big massive gel and the whole system results, in many cases, in a non-uniform one. Moreover, there are not many different such polyvalent metal salts that are hardly soluble in water. It is also possible to increase the vigor of the stirring on mixing the gelating agent. To increase the stirring, however, a special powerful stirring apparatus is required. Moreover, the product obtained by such powerful stirring is found, upon microscopic inspection to be nothing but a rather non-uniform one in which solid massive precipitates are divided into and dispersed in the form of fine granules.

We have, after studying processes for uniformly gelating CMC, found a process for preparing a very uniform and stable CMC gel, without using any special powerful stirring apparatus, by reacting CMC with a variety of water-soluble polyvalent metal salts, and have confirmed that the CMC gel so obtained is applicable for many practical uses including preparations of medicines, cosmetics and the like.

That is to say, we have succeeded in obtaining a very uniform and stable CMC gel free from solid mass or precipitates, by adding CMC wetted by or dispersed in a hydrophilic organic liquid compatible with water into an aqueous solution containing a water-soluble polyvalent metal salt.

It is considered that the gelation of CMC by a polyvalent metal salt is, in essence, a cross linking reaction by ionic bonds between the carboxyl groups of the CMC molecule and the polyvalent metal ions. In an aqueous solution prepared by dissolving CMC in water, almost all the molecules of CMC are uniformly dispersed and dissolved in water and so the carboxyl groups of CMC are in a highly reactive state by dissociation, for example, of sodium ions. Therefore, when a water-soluble polyvalent metal salt dissolved in water or in the form of powder is added to such an aqueous CMC solution, solid massive precipitates are formed in part and the gel obtained is not uniform, because the gelation velocity of CMC with the metal salt is much higher than the diffusion velocity of the metal salt. The gelation is not uniform when an aqueous solution of CMC is added to an aqueous soluton of a polyvalent metal salt, for the same reason.

On the other hand, neither precipitation nor gelation occurs at all when CMC and a water-soluble polyvalent metal salt are added to a hydrophilic organic liquid. This is because CMC is not dissolved and not dissociated into salt-forming ions. Only when water is added to such a mixture does the CMC dissolve and react with the metal salt to form a gel. Also in this case, however, the gel obtained is not uniform.

We have now determined that it is necessary to make the diffusion velocity of CMC and metal salt into the system higher than the dissolution velocity of CMC into water and the reaction velocity of CMC with metal salt, and found that organic liquids are available as an agent for retarding the dissolution and gelation of CMC.

That is, CMC particles whose surface is covered with a hydrophilic organic liquid are not quickly dissolved or gelated when they are added to an aqueous solution containing a metal salt. In this case, substitution of the organic liquid by water occurs first, and it takes from several seconds to several tens of seconds. Then, the CMC particles covered with water are dispersed and dissolved in water from their surface, and the molecules of CMC are dissolved. The CMC molecules thus dissolved react instantly with the polyvalent metal ions and gelation occurs. Thus there is a period of time of several tens of seconds or more until gelation occurs, after the addition of the CMC is dispersed in a hydrophilic organic liquid into the aqueous polyvalent metal salt solution, and accordingly it becomes possible to effect uniform dispersion and mixing for such period of time, without using any special powerful stirring apparatus, to obtain a uniform and stable gel.

SUMMARY OF THE INVENTION

The present invention provides stable gel compositions comprising a water-soluble salt of carboxymethyl cellulose wetter by or dispersed in a hydrophilic organic liquid and an aqueous solution containing a water-soluble polyvalent metal salt, and a process for the preparation of stable gel compositions comprising adding a water-soluble salt of carboxymethyl cellulose wetted by or dispersed in a hydrophilic organic liquid to an aqueous solution containing a water-soluble polyvalent metal salt, to obtain a uniform gel composition.

The stable gel compositions of the present invention are useful for many purposes including preparation of medicines, cosmetics and the like.

DESCRIPTION OF THE PREFERRED EMBODIMENTS

The present invention will now be explained in detail, referring to the preferred embodiments.

Although there is no special limitation on each component of the compositions of this invention since they are applicable for a variety of uses, the four components; water, water-soluble polyvalent metal salt, hydrophilic organic liquid and water-soluble salt of carboxymethyl cellulose, are essential for the compositions of the present invention. Besides these four essential components, one, two or more ingredients which are necessary for the use of each composition, that is, the main ingredient and/or the auxiliary ingredients, may be added to the compositions of the present invention.

As the water-soluble salt of carboxymethyl cellulose (CMC) used in the present invention, there can be mentioned for example sodium carboxymethyl cellulose, potassium carboxymethyl cellulose, ammonium carboxymethyl cellulose and the like. There is no special limitation on the degree of substitution of carboxymethyl (DS) and the viscosity (degree of polymerization) of the CMC, as long as it is soluble in water. The CMC may be selected from those having a degree of substitution within the range of 0.3-2.8 and a viscosity within the range of approx. 500 cps per 10% aqueous solution to approx. 500 cps per 1% aqueous solution, in accordance with the intended use and purpose. There is no special limitation also on the grain size of the CMC. Any commercially available fine powder which passes through a sieve of 80 mesh and rough granules of 30-80 mesh can be used.

As the water-soluble polyvalent metal salt used in the present invention, there can be mentioned aluminum salts such as aluminum acetate (soluble, or basic), aluminum sulfate, potassion alum, aluminum chloride, etc., iron salts such as ferrous chloride, ferric chloride, ferric sulfate, etc., cupric salts such as cupric chloride, cupric sulfate, etc., and other inorganic or organic magnesium salts, barium salts, calcium salts, manganese salts, cadmium salts, chromates, titanates, antimonates and so on. Any one or a mixture of two or more of these water-soluble polyvalent metal salts is selected and used in accordance with the final use of the composition obtained. It is desirable to select a non-toxic sale, when the composition is used as a medicine.

As the hydrophilic organic liquid used in the present invention, there can be mentioned aliphatic polyols such as glycerol, 1,3-butanediol, 1,4-butanediol, propanediol, ethylene glycol, polyethylene glycol, etc., aliphatic alcohols such as methyl alcohol, ethyl alcohol, propyl alcohol, butyl alcohol, etc., aliphatic ketones such as acetone, methyl ethyl ketone, etc., aliphatic acid esters such as methyl acetate, ethyl formate, ethyl propionate, etc., and other organic liquids compatible with water. Any one or a mixture of two or more of these hydrophilic organic liquids may be used.

There is no special limitation on the ratio of each component in the gel compositions of the present invention, which may be different in accordance with the intended use of individual compositions. However, the ratio is generally within the following range. The water-soluble polyvalent metal salt comprises 0.01-50 parts by weight and the water-soluble salt of carboxymethyl cellulose (CMC) comprises 0.01-50 parts by weight, per 100 parts by weight of water, and the ratio by weight of the hydrophilic organic liquid/CMC is within the range of 0.2-100.

When the amount of the water-soluble polyvalent metal sald added to 100 parts by weight of water is less than 0.01 part by weight, the degree of gelation is not sufficient. Its upper limit is usually about 50 parts by weight, although it depends on the solubility of the water-soluble polyvalent metal salt in water. The gelation is not sufficient also when the amount of CMC is less than 0.01 part by weight per 100 parts by weight of water, while more than 50 parts by weight of the CMC do not give a uniform gel. When the ratio by weight of the hydrophilic organic liquid/CMC is less than 0.2 there is a tendency for the resulting gel to become non-uniform while a ratio of more than 100 does not give a gel having a desirable hardness.

As examples of the uses or the objects to which the present invention are applied, there can be mentioned a wide variety of objects including medicines such as bases for stupes, bases for cataplasms, bases for analgesic/antiphlogistic/antispasmodic gels for external use, bases for aromatics, etc,; cosmetics such as cosmetic base cream, skin conditioning cream, vanishing cream, cold cream, bases for beauty pack, tooth-paste, shaving cream, permanent-waving agent, manicure, paste powder, cheek rouge, hair-dye, eyeliner, hair-setting lotion, etc.; additives for food such as pudding, jelly, etc.; mud-flow preserving agents for civil engineering works or oil-well drilling; gel electrolytes for battery; coating agents for wire and cable; and so on. In each of thes uses, a very uniform gel may be formed according to the present invention.

In practically applying the gel composition of this invention to these objects, the main ingredient and/or the auxiliary ingredient necessary for each object are added to the composition. For example, in the case of cataplasms, kaolin powder as the main ingredient and boric acid, methyl salicylate, peppermint oil and thymol, as the auxiliary ingredients, may be used, and it is desirable to use glycerol as the hydrophilic organic liquid. In the case of medicinal gels for external use, medicines having analgesic, antiphlogistic or antispasmodic activity may be used as the main ingredient and an auxiliary ingredient such as an aromatic may be added thereto.

In the case of a beauty pack, zinc white, kaolin, liquid paraffin, polyvinyl alcohol, etc. may be used as the main ingredient, and perfumes, preservatives, etc. as the auxiliary ingredient.

Although two or three representative examples have been mentioned above, any main ingredient and auxiliary ingredient therefor which are known in the field of each given use may be properly selected and used in a ratio known in the same field.

The present invention is further explained in detail in the following Examples. However, the invention is not limited to these Examples.

EXAMPLE 1

Potassium alum $[K_2Al_2(SO_4)_4.24H_2O]$ (0.5 g) was dissolved in water (200 g). Sodium carboxymethyl cellulose (DS=0.85, viscosity of 1% aqueous solution $\eta=100$ cps) (2 g) was wetted by glycerol (specific gravity=1.252) (10 g) and then added to the above aqueous potassium alum solution while stirring gently with a glass rod.

No partially solid mass was at all formed, and the viscosity increased smoothly as shown in Table 1 while the system was left to stand. The gelation progressed while the system was kept in the form of a solution. After standing overnight, the formed gel did not show any syneresis and was a somewhat elastic, uniform gel.

For a comparison of the uniformity of the gel, another preparation was prepared under the same conditions as mentioned above and, after 5 minutes, the preparation was filtered with an 8 mesh screen. Only 6 g remained on the screen and 205 g passed through it. Moreover, the gel remaining on the 8 mesh screen was not a solid massive one, but was very uniformly swelled.

TABLE 1

| Time after the preparation was left to stand (hr) | 0.25 | 1 | 2 | 3 | 20 |
|---|---|---|---|---|---|
| Viscosity of the system (cps, 25° C.) | 320 | 660 | 2,300 | 2,950 | 13,500 |

COMPARATIVE EXAMPLE 1

Sodium carboxymethyl cellulose (DS=0.85, $\eta=100$ cps) (2 g) was dissolved in water (190 g) and, to the solution there was added potassium alum (0.5 g) dissolved in water (10 g) while stirring gently in the same manner as Example 1.

A large quantity of a partially solid massive gel was formed just after the addition, and the system resulted in a substantially non-uniform gel. Although the viscosity of the system increased as the time it was left standing passed, the massive gel formed on preparation remained as it was and the whole system was a non-uniform gel of island-pattern even after one night.

For comparison of the uniformity of the gel, the preparation was filetered with an 8 mesh screen just after (after 5 minutes) it was prepared. A solid massive gel remaining on the screen amounted to 60 g. Thus the resulting gel was not a uniform one, quite different from that obtained in Example 1.

EXAMPLES 2–4

In accordance with the method of Example 1, other kinds of sodium carboxymethyl celluloses were examined. The sodium carboxymethyl cellulose used in each Example was as follows:

| Example | CMC DS | Viscosity of 1% aqueous solution |
|---|---|---|
| 2 | 0.67 | 180 cps |
| 3 | 1.35 | 150 cps |
| 4 | 2.47 | 25 cps |

Also in the case of these sodium carboxymethyl celluloses, the amount of gel remaining on an 8 mesh screen by filtration effected 5 minutes after preparation was quite small as shown in the following Table 2, that is, quite uniform gelation occured.

TABLE 2

| Example No. | 2 | 3 | 4 |
|---|---|---|---|
| Amount of gel on the screen (g) | 3 | 4 | 0.5 |

EXAMPLE 5

In accordance with the method of Example 1, 1,3-butanediol was used instead of glycerol.

Also in this case, no solid mass was formed just after preparation, as in Example 1. The viscosity increased smoothly as shown in Table 3, and the gel formed was a uniform one showing no syneresis.

TABLE 3

| Time after the preparation was left to stand (hr) | 0.25 | 1 | 2 | 3 | 96 |
|---|---|---|---|---|---|
| Viscosity of the system (cps, 25° C.) | 1150 | 7930 | 12300 | 14900 | 18000 |

EXAMPLES 6–15

In accordance with the method of Example 5, other hydrophilic organic liquids were examined. The kinds of solvents used and the changes in viscosity accompanying gelation are shown in Table 4. In all these cases too, uniform gelation occured.

TABLE 4

| Example No. | Hydrophilic organic liquid used | Viscosity (cps) at each time after the Preparation was left to stand (hr) | | | | | |
|---|---|---|---|---|---|---|---|
| | | 0.25 | 1 | 2 | 3 | 24 | 96 |
| 6 | 1,4-butanediol | 790 | 4450 | 10100 | 11600 | — | 17000 |
| 7 | ethylene glycol | 830 | 5600 | 10140 | 11100 | 14960 | — |
| 8 | polyethylene glycol #200 | 1160 | 5900 | 10300 | 10800 | 15100 | — |
| 9 | polyethylene glycol #400 | 880 | 2700 | 7500 | 9500 | 15000 | — |
| 10 | polyethylene glycol #600 | 980 | 6650 | 10200 | 11880 | 15000 | — |
| 11 | methyl alcohol | 560 | 1330 | 1750 | 3550 | 13000 | — |
| 12 | isopropyl alcohol | 630 | 2580 | 3540 | 5100 | 15000 | — |
| 13 | acetone | 540 | 790 | 1380 | 2800 | — | 16000 |
| 14 | methyl ethyl ketone | 600 | 870 | 2500 | 5500 | — | 15750 |
| 15 | methyl acetate | 560 | 1160 | 3800 | 6800 | 14100 | — |

EXAMPLE 16

In accordance with the method of Example 1, soluble aluminum acetate was used instead of potassium alum.

The gel remaining on an 8 mesh screen by filtration effected 5 minutes after preparation weighed only 7 g, and it was not a solid massive one but a uniformly swelled one. The changes in viscosity of the system, which accompanied the progress of gelation, are shown in Table 5.

TABLE 5

| Time after the preparation was felt to stand (hr) | 0.25 | 1 | 2 | 3 | 96 |
|---|---|---|---|---|---|
| viscosity of the system (cps, 25° C.) | 620 | 2450 | 10500 | 12400 | 18500 |

EXAMPLES 17–19

Cupric chloride ($CuCl_2.2H_2O$) (0.5 g) was dissolved in water (100 g). To this aqueous solution of cupric chloride, each of the following three kinds of sodium carboxymethyl cellulose having viscosities different from each other (2.5 g) dispersed in glycerol (10 g) was added while gently stirring the solution.

In this case, no partially solid mass was at all formed and uniform gelation occured. The changes in viscosity of the system, which accompanied the progress of gelation, are shown in Table 6.

TABLE 6

| Example No. | Sodium carboxymethyl cellulose | | Viscosity (cps) after preparation | |
|---|---|---|---|---|
| | DS | Viscosity of 1% aqueous solution | 0.25 hr | 48 hr |
| 17 | 0.96 | 24 cps | 730 | 9000 |
| 18 | 0.97 | 550 cps | 950 | 31000 |
| 19 | 0.97 | 1830 cps | 1890 | 35000 |

EXAMPLE 20

In accordance with the method of Example 18, ferric chloride ($FeCl_3.6H_2O$) was used instead of cupric chloride.

In this case also, it was confirmed that no solid mass was formed and uniform gelation occured.

EXAMPLE 21

Kaolin (10 g) and potassium alum (1 g) were added to water (119 g) and mixed. To the suspension which was obtained, sodium carboxymethyl cellulose (DS=1.25, $\eta$=35 cps) (10 g) dispersed in glycerol (60 g) was added while stirring gently.

No solid massive gel was at all formed and a uniform gel having very smooth surface and section was formed. The changes in viscosity of the system, which accompanied the progress of gelation, are shown in Table 7.

TABLE 7

| Time after the preparation was left to stand (hr) | 0.25 | 1 | 2.5 | 5 | 7.5 | 24 | 96 |
|---|---|---|---|---|---|---|---|
| Viscosity of the system (cps, 25° C.) | 21000 | 46000 | 72000 | 120000 | 195000 | 710000 | 1750000 |

COMPARATIVE EXAMPLE 2

The procedure of Example 21 was carried out using the same components in the same amounts, but changing the order of addition. That is, sodium carboxymethyl cellulose (10 g) was dissolved in water (119 g) and, to the obtained aqueous solution a mixture of kaolin (10 g), glycerol (60 g) and potassium alum (1 g) was added while stirring gently.

A large amount of solid massive gel having 5-10 mm$\phi$ was formed just after preparation and non-uniform gelation occured. The changes in viscosity which accompanied the progress of gelation are shown in Table 8. As can be seen therefrom, the apparent viscosities were quite low as compared with these of Example 21 and the gel obtained was a non-uniform gel having an island-pattern.

TABLE 8

| Time after the preparation was left to stand (hr) | 0.25 | 1 | 2.5 | 5 | 7.5 | 24 | 96 |
|---|---|---|---|---|---|---|---|
| viscosity of the system (cps, 25° C.) | 25000 | 24000 | 25000 | 26000 | 27000 | 47000 | 110000 |

EXAMPLE 22

Sodium carboxymethyl cellulose (1 g) was dispersed in glycerol (5 g) and the dispersion was added to water (84 g) containing sodium cetylsulfate (0.1 g) and calcium hydroxide (0.5 g) while stirring. Further, tincture of benzoin (5 g), ethyl alcohol (5 g), phenol (0.05 g) and perfume (0.5 g) were added to the mixture. A cosmetic milky lotion of uniform jelly was obtained.

EXAMPLE 23

A black dyestuff (1 g) (containing lead) and citric acid (1 g) were dissolved in water (65 g) and, to the solution, sodium carboxymethyl cellulose (5 g) dispersed in isopropyl alcohol (20 g) and benzyl achohol (5 g) was added. A good, sticky hair-dye was obtained.

EXAMPLE 24

Sodium carboxymethyl cellulose (3 g) and polyvinyl alcohol (7 g) were dispersed in glycerol (10 g) and ethyl alcohol (10 g), and the dispersion was added to water (60 g) containing alum (0.1 g) and perfume (0.5 g), while stirring. A good beauty pack was obtained, which formed a uniform coating having a smooth surface, when spread on a glass plate. It was easily peeled off after being dried.

EXAMPLE 25

Calcium phosphate (dihydrate) (45 g), sorbitol (10 g), sodium laurylsulfate (2 g), silicic anhydride (2 g), aluminum hydroxide (0.2 g) and perfume (1 g) were added to water (3 g), and to the mixture was added further a dispersion of sodium carboxymethyl cellulose (1 g) in glycerol (10 g). The product obtained was of good quality for tooth paste, having a very smooth and glossy surface and section.

What is claimed is:

1. A stable gel composition which is prepared by a process comprising adding a water-soluble salt of carboxymethyl cellulose selected from the group consisting of sodium carboxymethyl cellulose, potassium carboxymethyl cellulose and ammonium carboxymethyl cellulose which has previously been wetted by or dispersed in a hydrophilic organic liquid selected from the group consisting of an aliphatic polyol, a lower aliphatic alcohol, an aliphatic ketone and a fatty acid ester to an aqueous solution containing a water-soluble polyvalent metal salt selected from the group consisting of an aluminum salt, an iron salt and a cupric salt, wherein the water-soluble salt of carboxymethyl cellulose and the water-soluble polyvalent metal salt are both present in amounts of 0.01-50 parts by weight per 100 parts by weight of water contained in the aqueous solution and the weight ratio of hydrophilic organic liquid to water-soluble salts of carboxymethyl cellulose is 0.2-100:1.

2. A gel composition as claimed in claim 1 wherein the aliphatic polyol is selected from the group consisting of glycerol, 1,3-butanediol, 1,4-butanediol, propanediol, ethylene glycol and polyethylene glycol, the lower aliphatic alcohol is selected from the group consisting of methyl alcohol, ethyl alcohol, propyl alcohol and butyl alcohol, the aliphatic ketone is selected from the group consisting of acetone and methyl ethyl ketone, and the fatty acid ester is selected from the group consisting of methyl acetate, ethyl formate and ethyl propionate.

3. A gel composition as claimed in claim 1 wherein the aluminum salt is selected from the group consisting of aluminum acetate, aluminum sulfate, potassium alum and aluminum chloride, the iron salt is selected from the group consisting of ferrous chloride, ferric chloride and ferric sulfate, and the cupric salt is selected from the group consisting of cupric chloride and cupric sulfate.

4. A gel composition as claimed in claim 1 and further comprising an additional ingredient to be dispersed or dissolved in the gel and/or an auxiliary ingredient therefor both of which are pre-selected depending upon the ultimate use of the composition, and are previously added to either the aqueous solution containing a water-soluble polyvalent metal salt or the water-soluble salt of carboxymethyl cellulose wetted by or dispersed in a hydrophilic organic liquid.

5. A gel composition as claimed in claim 4 wherein the main ingredient and/or the auxiliary ingredient are for cosmetic use.

6. A gel composition as claimed in claim 4 wherein the main ingredient is an analgesic, antiphlogistic or antispasmodic agent which can be externally used and the auxiliary ingredient is an auxiliary ingredient for said agent.

7. A gel composition as claimed in claim 6 and which is used for cataplasms.

8. A gel composition as claimed in claim 1 wherein the water-soluble salt of carboxymethyl cellulose and the water-soluble polyvalent metal salt are present respectively in amounts of about 1 part by weight and about 0.25 part by weight per 100 parts by weight of water contained in the aqueous solution and the weight ratio of hydrophilic organic liquid to water-soluble salts of carboxymethyl cellulose is about 5:1.

* * * * *